United States Patent [19]

Handrick et al.

[11] 4,440,957

[45] Apr. 3, 1984

[54] PREPARATION OF β-ISOPROPYLNAPHTHALENE

[75] Inventors: Kurt Handrick; Georg Kölling; Paul Kiedel, all of Essen, Fed. Rep. of Germany

[73] Assignee: Bergwerksverband GmbH, Essen, Fed. Rep. of Germany

[21] Appl. No.: 289,525

[22] Filed: Aug. 3, 1981

Related U.S. Application Data

[63] Continuation of Ser. No. 136,968, Apr. 3, 1980, abandoned, which is a continuation of Ser. No. 7,406, Jan. 29, 1979, abandoned, which is a continuation of Ser. No. 842,841, Oct. 3, 1977, abandoned.

[30] Foreign Application Priority Data

Oct. 2, 1976 [DE] Fed. Rep. of Germany ....... 2644624

[51] Int. Cl.³ .......................... C07C 2/68; C07C 5/22
[52] U.S. Cl. .................................. 585/323; 585/320; 585/466; 585/477
[58] Field of Search ............... 585/320, 323, 477, 466

[56] References Cited

U.S. PATENT DOCUMENTS

| | | | |
|---|---|---|---|
| 3,458,587 | 7/1969 | Suld | 585/466 |
| 3,504,045 | 3/1970 | Scharf et al. | 585/477 |
| 3,813,451 | 5/1974 | Canfield et al. | 585/466 |

*Primary Examiner*—Curtis R. Davis
*Attorney, Agent, or Firm*—Michael J. Striker

[57] ABSTRACT

Process of preparing β-isopropylnaphthalene substantially free of corresponding α-isomer, in yields amounting to 90% and more by a continuous two-stage process comprising (1) alkylating naphthalene with propylene at a temperature of about 150°–280° C. under a pressure of 5 to 30 atm in the presence of a phosphoric acid catalyst supported on a $SiO_2$ carrier and using a mol ratio of 1/5 to 1/20 mol propylene to 1 mol naphthalene to isopropylate 45 to 65% of the naphthalene and form a mixture of α- and β-isopropylnaphthalene and then without separating off the unreacted naphthalene, (2) heating the isomeric mixture from stage (1) in the presence of a phosphoric acid catalyst supported on $SiO_2$, to a temperature of 180°–280° C. under an inert gas pressure of 5 to 30 atm until no further β-isopropylnaphthalene is formed and recovering said β-isopropylnaphthalene from the isomerization mixture.

10 Claims, 5 Drawing Figures

PREPARATION OF β-ISOPROPYLNAPHTHALENE

This is a continuation of application Ser. No. 136,968, filed Apr. 3, 1980 which in turn is a continuation of application Ser. No. 007,406, filed Jan. 29, 1979, which in turn is a continuation of application Ser. No. 842,841, filed on Oct. 3, 1977 all of which are now abandoned.

This invention relates to a process for the preparation of β-isopropylnaphthalene by alkylation of naphthalene with propylene in the presence of a phosphoric acid catalyst on silicon dioxide as carrier. More particularly, this invention relates to a continuous two-stage process for preparing β-isopropylnaphthalene in greater than 90% yields. Still more particularly, this invention relates to a process for the preparation of β-isopropylnaphthalene in high yield and purity by a two-stage process, i.e. alkylation and isomerization carried out in the presence of acid catalysts.

It is already known to catalytically alkylate naphthalene with propylene to form an isomeric mixture of α- and β-isopropylnaphthalene. If it is desired to prepare β-isopropylnaphthalene to the substantial exclusion of its corresponding α-isomer, this can be done by the catalytic after treatment of the isomeric mixture obtained by alkylation to increase the amount of the β-isomer at the expense of the α-isomer co-formed in such alkylation reaction. However large amounts of by-products are produced in the isopropylation and isomerization including diisopropylnaphthalene, polyisopropylnaphthalene and additional unidentifiable condensation products present in a tarry condition or state. It is generally necessary for most chemical reactions that the β-isomer of isopropylnaphthalene be present substantially uncontaminated by such by-products and also by its α-isomer. Thus when the β-isopropylnaphthalene is used in the preparation of β-naphthol and acetone, the presence of the α-isomer substantially interferes with the reation.

Methods whereby to achieve the maximum formation of the β-isomer from naphthalene have been proposed. Thus, for example, in U.S. Pat. No. 3,458,587, there is described a process for preparing β-isopropylnaphthalene by the alkylation of naphthalene with propylene over a solid phosphoric acid-kieselguhr catalyst activated with water or an alcohol, under pressure and at a temperature of 150°-350° C., preferably 260°-300° C., in the presence of a large quantity of a solvent and using in such alkylation reaction a mol ratio of naphthalene to propylene of 1:1 to 2:1. This alkylation is followed by isomerization of the isomeric mixture, but only after distillative separation of the unreacted naphthalene. The isomerization is conducted by contacting the isomeric mixture with anhydrous hydrofluoric acid as the isomerization catalyst, again in the presence of a solvent.

There are formed in this process relatively large amounts of byproducts. Further it has not been possible to carry out this process in a continuous fashion or in an economically feasible manner. Still further, having to operate with the large amounts of solvent required, considerably hinders the process and contributes to making it commercially unacceptable.

This invention has an object to provide a process for preparing β-isopropylnaphthalene of a high degree of purity.

Another object of the invention is to provide a process whereby the yield of the isomeric mixture of α- and β-isopropylnaphthalene obtained by alkylation of naphthalene with propylene is increased and also where there are obtained in the subsequent isomerization, higher yields of β-isopropylnaphthalene at the expense of the α-isopropylnaphthalene.

Still another object of the invention is an alkylation-isomerization process for producing β-isopropylnaphthalene substantially free of unwanted diisopropylnaphthalene, polyisopropylnaphthalene and the like.

It is yet a further object of the invention to provide a process wherein the alkylation-isomerization can be carried out continuously, and more especially where a distillative separation of the formed isomeric mixture from the unreacted naphthalene becomes unnecessary.

These and other objects and advantages of the invention by the instant process comprises (1) alkylating naphthalene with propylene in the presence of a phosphoric acid catalyst supported on $SiO_2$, at a temperature of 150°-280° C. and a pressure of 5-30 atm. using a mol ratio of 1/5 to 1/20 mol propylene per 1 mol of starting naphthalene, until in the reaction 45 to 65% of the naphthalene has been isopropylated and then without separating off the unreacted naphthalene, (2) further treating the alkylation mixture by heating it in the presence of a phosphoric acid catalyst supported on $SiO_2$ under an inert gas pressure of 5 to 30 atm. to a temperature of 180° to 280° C. until substantially no more β-isopropylnaphthalene is formed from the α-isopropylnaphthalene. There is thereby obtained an isomeric mixture consisting of 90-95% of the β-isopropylnaphthalene isomer. Pure β-isopropylnaphthalene can be recovered from this isomeric reaction product by distillation and crystallization.

In the instant invention, the use of the propylene in very small quantities as compared to the quantity of naphthalene results the unexpected but highly advantageous result that the exotherm generated by the reaction does not result in high temperature increases which in turn act to considerably increase the amount of undesirable by-products formed.

Interruption of the isopropylation after only a 45 to 65% conversion of the naphthalene has taken place has the advantageous result that the formation of undesirable by-products, especially of diisopropylnaphthalene is avoided, this taking place much more readily once an about 50% naphthalene conversion has been reached. The presence of the higher naphthalene content in the alkylation products produced in the first stage has the result that in the following isomerization, by-product formation is decreased so that there is obtained a very good yield of the β-isopropylnaphthalene.

In the drawings which form a part of this application:

Figure 1:
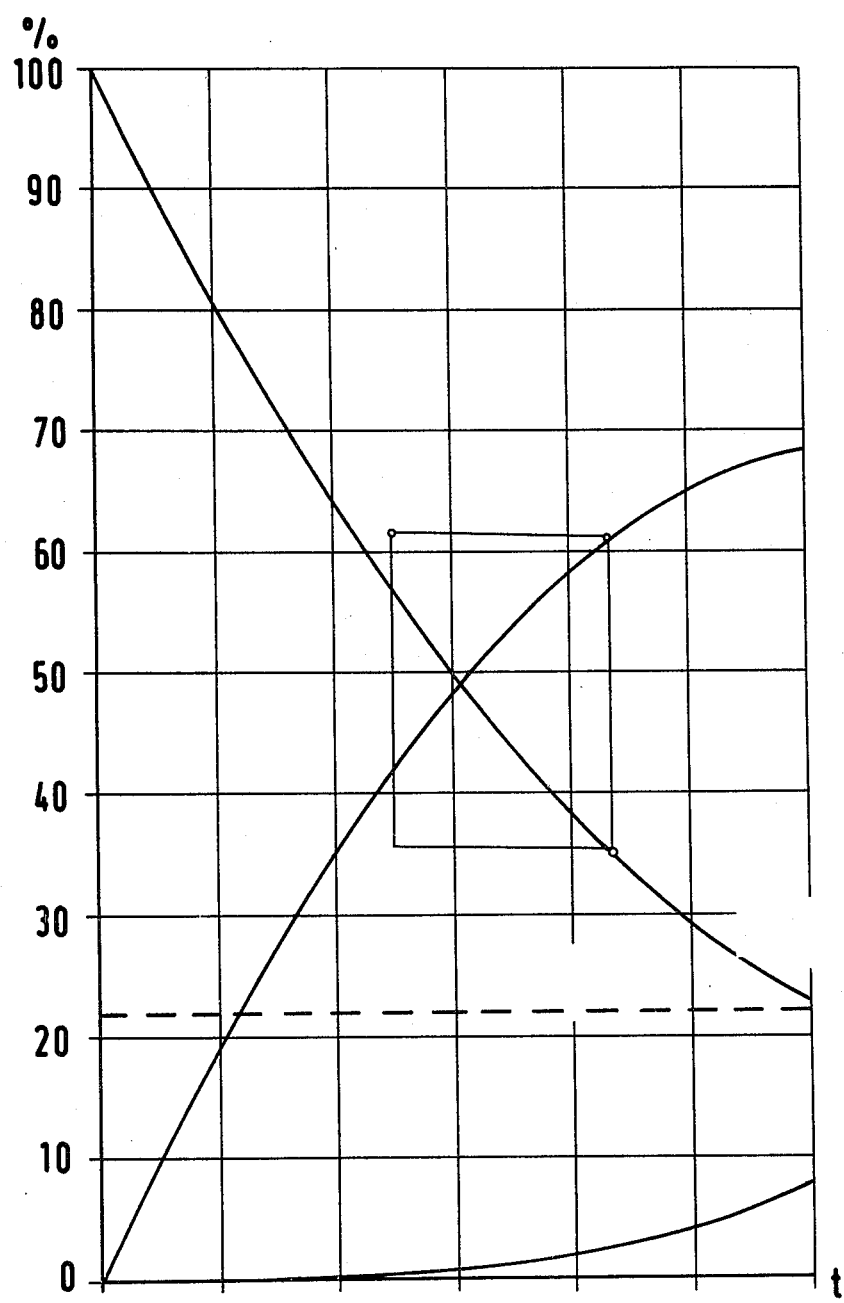
FIG. 1 is a graph showing the course of the isopropylation of naphthalene under the following conditions: mol ratio naphthalene:propylene—5:1; temperature—150° C.; pressure—20 atm.

The process of the invention is carried out by conducting liquid naphthalene through a number of sequentially arranged reactors. There can be 3 to 15 and preferably 4 to 8 of such reactors each filled with the solid acid catalyst. The propylene in the calculated amounts is introduced into and conducted through the reactors operated under pressure. In order to provide for an easily regulatable charging rate and to achieve a positive flow in the reactors and namely to ensure that a satisfactory working pressure exists and also for moderating the exotherm of the reaction, the propylene is diluted with an inert gas, for instance, propane, nitrogen or CO$_2$. In the subsequent isomerization, which may also be carried out in a multiple number of reactors, an inert gas, such as N$_2$ is conducted through the reaction mixture.

The velocity of the reaction in the alkylation stage depends on the pressure, temperature and naphthalene/propylene mol ratio in use. Generally, in each reactor only 1 mol of propylene is introduced for every 10–20 mols naphthalene. The use of temperatures of 200°–240° C. and of pressures of 10–25 atm. also results in excellent yields being obtained in the range of the process conditions of the invention.

The number of steps involved in the introduction of the propylene is determined by the amount of propylene used and also to some extent on the other conditions. When 1/20 mol propylene is used per 1 mol naphthalene then about 8–12 steps are required in order to realize a 50% conversion; in the case of 1/5 mol propylene per 1 mol naphthalene, only 2–4 steps are necessary.

At a mol ratio of naphthalene to propylene of 10:1, a working time of 5 hours is required to convert about 50% of the naphthalene. The first stage of alkylation generally takes 2–8 and preferably 4–6 hours.

Depending on the β-isopropylnaphthalene content in the alkylation product obtained from stage 1, there is required in the second or isomerization stage, a reaction time of 1½–5 hours and preferably from 2–4 hours in order to bring the β-isopropylnaphthalene content in the isomeric mixture to a value of 90–95%.

Most advantageously, the isopropylation and the isomerization stages are both carried out under the same temperatures and pressures.

Phosphoric acid catalysts supported on SiO$_2$ which are suitable for use in the process of the invention have been described in U.S. Pat. No. 3,458,587 at column 3, lines 46–64 and column 4, lines 52–58. The catalysts can be activated through contact with water or alcohol used in amounts of from about 100 to 3000 ppm based on the weight of the naphthalene. The catalysts can be purchased in Germany from the firm of Houdry Hüls GmbH under the designation #SH 60 17 and H 62 06; in the United States from Universal Oil Products. Basically the catalyst for both the alkylation and isomerization stages is a solid phosphoric acid or an inert carrier such as clay, kieselguhr, or the like, and is preferably kieselguhr containing from 10–20% free P$_2$O$_5$ (45–55% total P$_2$O$_5$).

The reaction course of the two stages of the process of the invention has been illustrated and further explained in the drawings briefly described above. As used in the drawings the terms as hereinafter set out have the indicated meanings: BIPN-β-isopropylnaphthalene α-/β-IPN-α-/β-isopropylnaphthalene, DIPN-diisopropylnaphthalene.

The graph (FIG. 1) illustrates that on reaching a yield of 68% α/β-IPN, only about 23% naphthalene remains unconverted. Simultaneously about 8% of the naphthalene is converted into the unwanted DIPN. Most significant is that the amount of β-IPN in the α/β-IPN mixture remains constant at 22% as can be seen by considering the broken or dashed line. From this graph it can also be seen that after 45–65% conversion of the naphthalene has taken place, (enclosed area) the formation of DIPN increases markedly so that terminating the isopropylation in the indicated conversion range is to be considered most advantageous.

Figure 2:
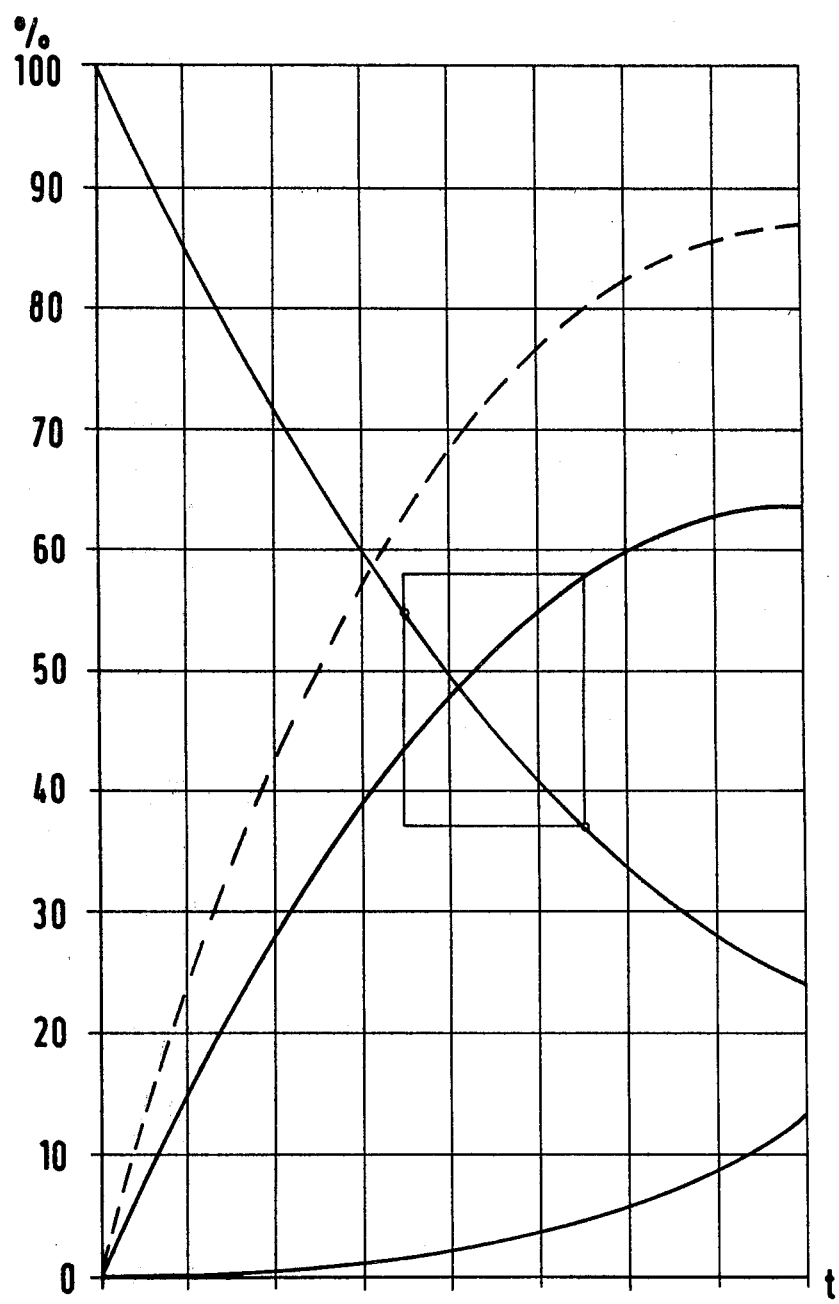
FIG. 2 is a graph showing the isopropylation of naphthalene under the following conditions: mol ratio naphthalene:propylene—10:1; temperature 240° C.; pressure—10 atm.

From the graph (FIG. 2) it can be seen that the formation of DIPN is greatly increased after an about 50% conversion of the naphthalene has occurred so that terminating the alkylation in the range of the enclosed area is advantageous. Most interestingly, the proportion of β-IPN in the α/β-IPN remains constant and amounts at a 50% naphthalene conversion to about 69%, and at an about 75% naphthalene conversion to about 88%. These relationships can be seen from a consideration of the dashed curve of this graph (FIG. 2).

Figure 3:
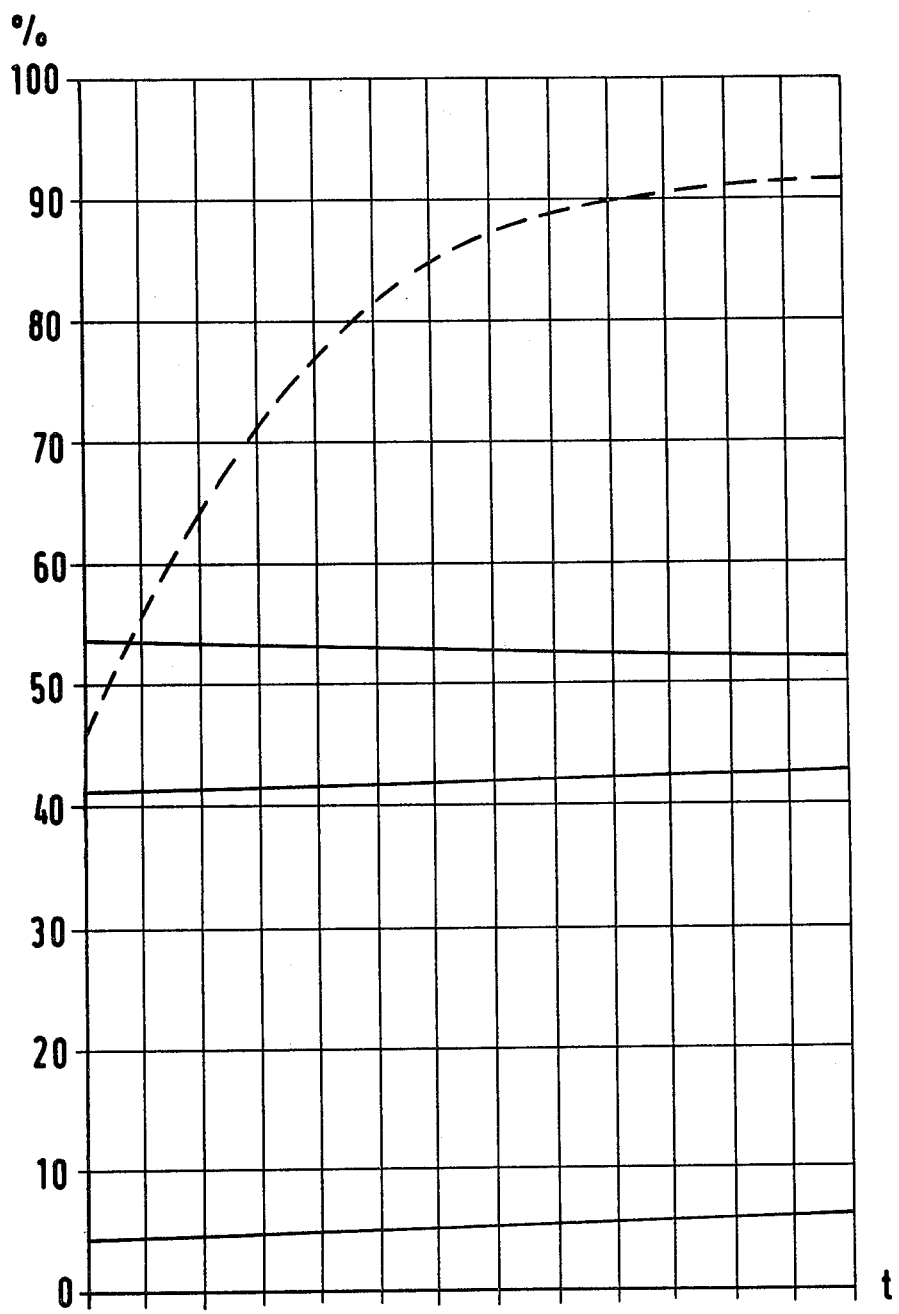
FIG. 3 is a graph showing the isomerization of an isopropylation product composed of 54.1% naphthalene, 41.4% isopropylnaphthalene (45.6% β-isopropylnaphthalene) and 4.5% diisopropylnaphthalene, under the following conditions: temperature—240° C.; pressure by charging nitrogen—10 atm.

The graph of FIG. 3 shows that the content of naphthalene and of isomeric mixture (α/β-IPN in the reaction mixture) is only immaterially changed as is the case for the DIPN content. Only the amount of β-IPN is important and this increases considerably to 92% in the aforesaid isomeric mixture.

Figure 4:
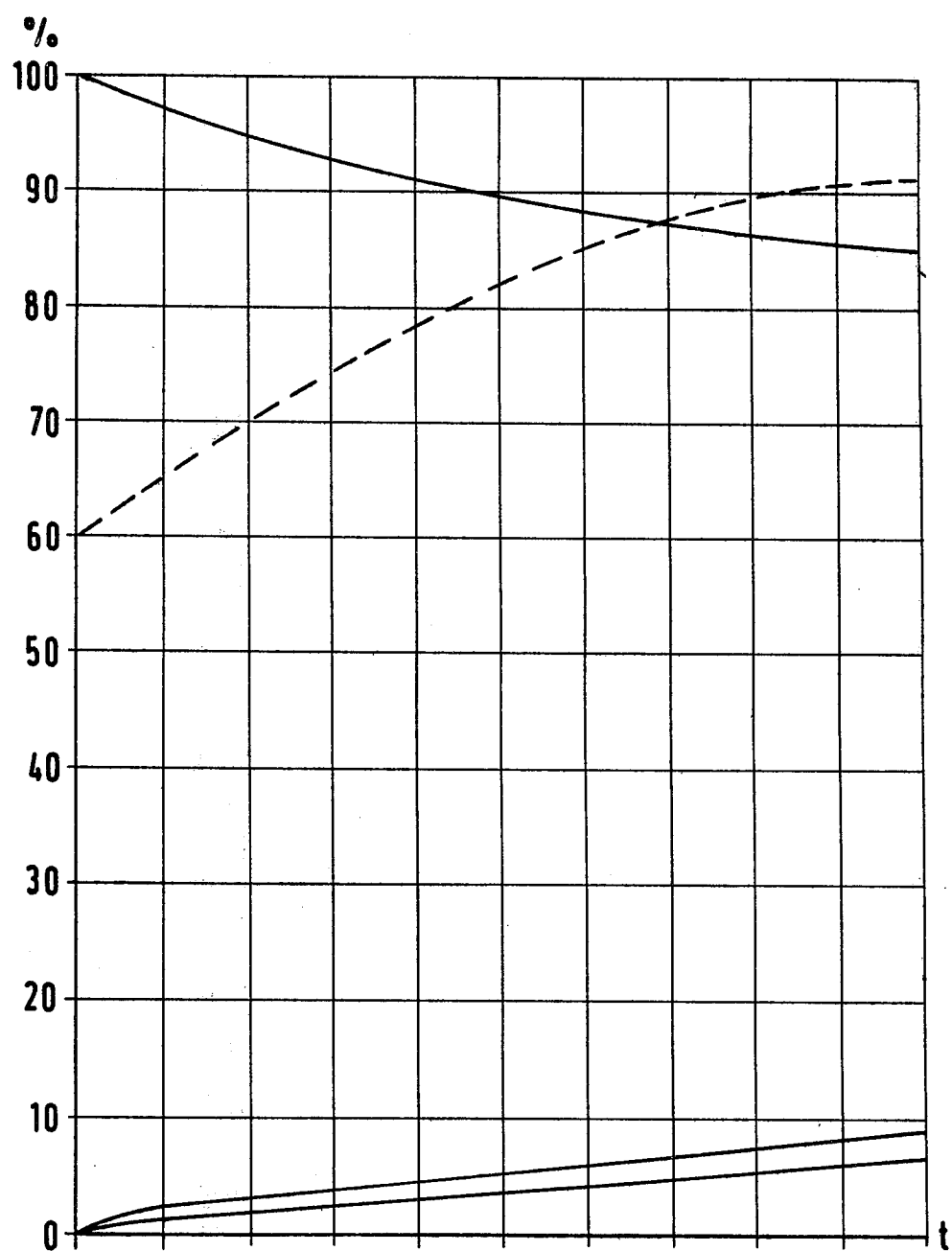
FIG. 4 is a graph showing the course of an isomerization of a distilled isomeric mixture of α- and β-isopropylnaphthalene having a β-isopropylnaphthalene content of 60.3% under the following conditions: Reactor temperature—200° C.; N$_2$-pressure—15 atm.

The graph of FIG. 4 illustrates that it is at the expense of the isomeric mixture formed that 6% of naphthalene and 9% of DIPN are newly formed by disproportionation reactions. At the same time, the β-IPN content in the isomeric mixture increases from 60–92%. Because of the increased tendency to form undesirable by-products it is recommended that the α/β-isopropylnaphthalene therefore not be distilled off from the reaction mixture.

Figure 5:
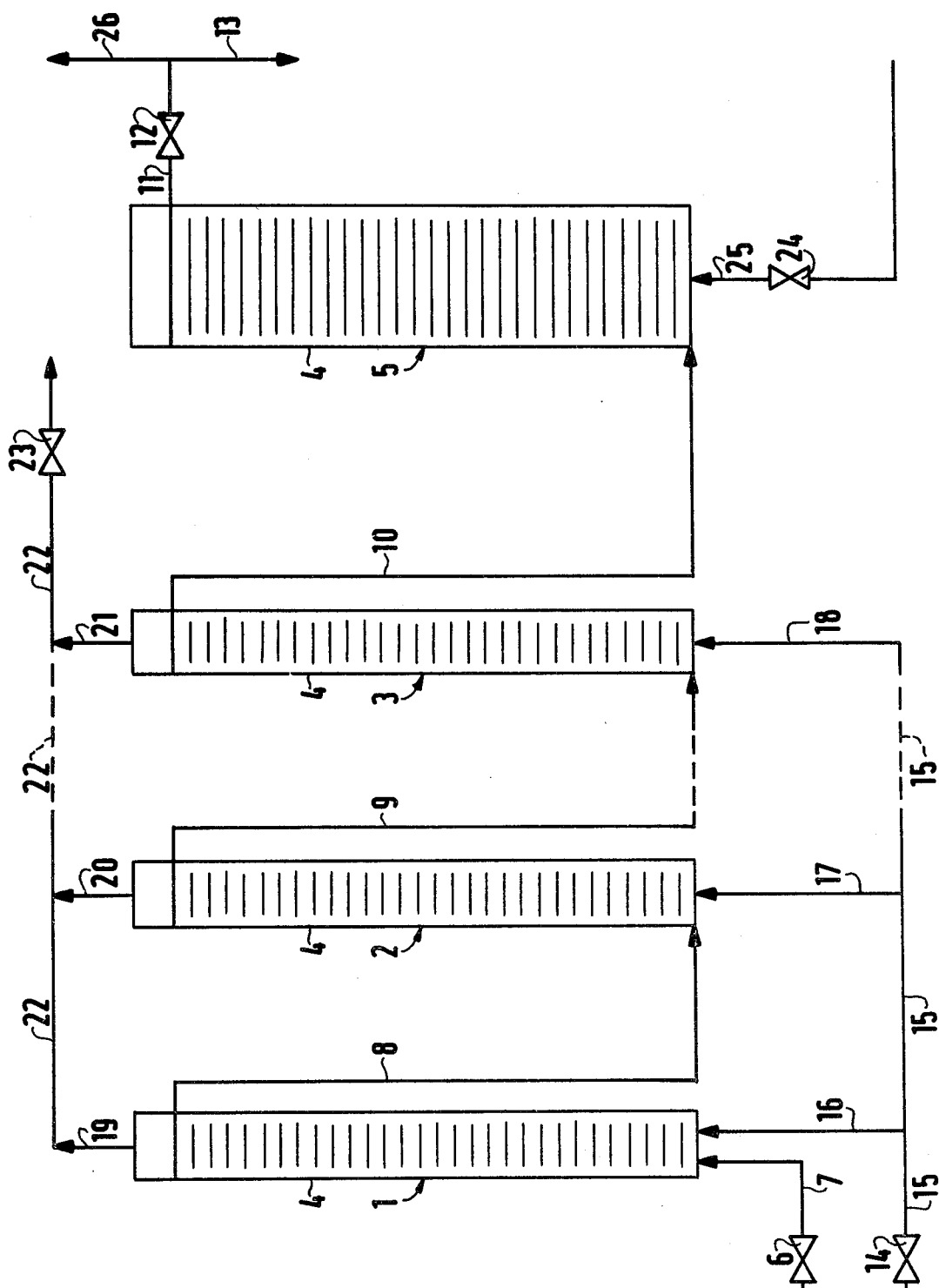
FIG. 5 illustrates diagrammatically an apparatus for carrying out the process of the invention.

The manner of carrying out the process of the invention in continuous fashion can be seen from FIG. 5.

As can be seen from this drawing, there are provided sequentially arranged isopropylation reactors 1, 2 and 3 which have been filled with phosphoric acid catalyst supported on kieselguhr 4. The same catalyst has also been filled into the subsequently arranged isomerization reactor 5. The reactors are constructed of pressure resistant steel and are provided with heating jackets (not shown).

The liquid naphthalene is pumped upwardly into reactor 1 through the valve 6 and pipe 7 and flows from the top of the reactor into and through pipe 8 into the bottom of reactor 2 and upwardly therethrough, out of the top of reactor 2 into and through pipe 9, thence into the bottom of reactor 3, upwardly therethrough, out through pipe 10 into isomerization reactor 5, from there over pipe 11, valve 12 and pipe 13 and out of the system.

For isopropylating the naphthalene, a gaseous mixture of propylene and propane is pumped through valve 14, pipes 15, 16, 17 and 18 into the bottom of reactors 1, 2 and 3 via pipes 19, 20, 21 and 22 respectively and valve 23.

The broken or dashed portions of the pipes 9, 15 indicate that additional reactors can be installed intermediate reactors 2 and 3.

For maintaining the desired overpressure in the isomerization reactor 5, an inert gas is introduced over valve 24 and pipe 25. The inert gas leaves reactor 5 together with the isomerization product via pipe 11, valve 12 and escapes under normal pressure from the isomerization reactor through pipe 26.

The present invention is further illustrated with respect to a specific embodiment thereof in the following example.

EXAMPLE

An isopropylation installation is provided composed of 5 reactors each having a height of 2 m and an inner diameter of 180 mm. Each reactor is filled with 40 liters phosphoric acid catalyst (6×6 mm strands) and the reactor heated to a temperature of 240° C. 40 kg (312.5 mol) molten naphthalene are introduced hourly into the system and simultaneously each hour per reactor, about 1.3 kg (31 mol) propylene and thus hourly 6.5 kg (156 mol propylene) are introduced upwardly into the likewise upwardly moving molten naphthalene so that in the melt in each of the reactors there is present 1 mol propylene for reaction with each 10 mols starting naphthalene. The pressure is maintained throughout at 10 atm.

Hourly there are discharged from the alkylation reactors a total of 46.3 kg reaction mixture and this is introduced into the isomerization reactor which has an inner diameter of about 200 mm and a length of 4 mm and which has been filled with phosphoric acid catalyst. The reactor temperature amounts to 240° C. and the pressure is held at 10 atm with $N_2$.

The duration or dwell time of the starting naphthalene in the first stage amounts to 5 hours and in the isomerization or second stage to about 2 hours. The mixture discharged from the isopropylation reactors has a composition of 48% naphthalene, 52% of α/β-IPN and 2% DIPN. The α/β-IPN contains 73% β-IPN.

After leaving reactor 5 the β-IPN content has been increased to 92% the DIPN amounts to about 3% and the naphthalene content has fallen to about 45%.

The isomerization product is then distilled in the conventional manner under vacuum and the naphthalene, α/β-isopropylnaphthalene and diisopropylnaphthalene recovered. The α/β-isopropylnaphthalene is crystallized out of methanolic solution under deep cooling and thereby a purified product obtained. There is thereby recovered pure β-isopropylnaphthalene having a melting point of 15.1° C.

We claim:
1. A continuous process for preparing β-isopropylnaphthalene comprising
   (a) alkylating naphthalene with propylene by introducing these two compounds into a multiplicity of reaction zones at a temperature between about 150° and 280° C. and a pressure between about 5 and 30 atm in the absence of a normally liquid solvent and in the presence of a phosphoric acid catalyst supported on a $SiO_2$, this introduction being effected in amounts to obtain a mol ratio of 1/5 to 1/20 mol of propylene to 1 mol of naphthalene in each reaction zone until 45 to 65% of the naphthalene are converted in the entire alkylating reaction to an isomeric mixture of α- and β-isopropylnaphthalene, then
   (b) charging said isomeric mixture into an isomerization zone wherein said mixture is heated to a temperature between about 180° and 280° C. at an inert gas pressure of between about 5 and 30 atm and in contact with said phosphoric acid catalyst supported on $SiO_2$ until no further β-isopropylnaphthalene is formed,
   (c) whereupon the β-isopropylnaphthalene is recovered from the isomerization zone at a purity of about 90 to 95%.
2. Process according to claim 1, wherein said alkylating is carried out at a temperature of 200°–240° C. and a pressure of 10–25 atm.
3. Process according to claim 1, wherein said alkylating is carried out for from 2 to 8 hours.
4. Process according to claim 1, wherein said alkylating is carried out for from 4–6 hours.
5. Process according to claim 1, wherein the isomerization is completed after 1½–5 hours.
6. Process according to claim 1, wherein the isomerization is completed after 2–4 hours.
7. Process according to claim 1, wherein the alkylating and isomerization are each carried out under the same temperature and pressure.
8. Process according to claim 1, wherein the alkylating is carried out in the presence of a catalyst activator selected from the group consisting of water and alcohol.
9. Process according to claim 1, wherein said propylene is diluted with an inert gas selected from the group consisting of propane, nitrogen and $CO_2$.
10. The process of claim 1 wherein the alkylation is carried to the point where an about 50% conversion of the naphthalene has occurred.

* * * * *